United States Patent [19]

Makower et al.

[11] Patent Number: 5,569,297
[45] Date of Patent: Oct. 29, 1996

[54] SELECTIVE VASCULAR COMPRESSION DEVICE

[75] Inventors: Joshua Makower, Nanuet; Brett Stern, New York, both of N.Y.

[73] Assignee: Schneider (USA) Inc., Plymouth, Minn.

[21] Appl. No.: 302,542

[22] Filed: Sep. 8, 1994

[51] Int. Cl.$^6$ ............................................. A61B 17/12
[52] U.S. Cl. ............................................. 606/201
[58] Field of Search ..................... 606/201–203

[56] References Cited

U.S. PATENT DOCUMENTS

| | | |
|---|---|---|
| 37,156 | 12/1862 | Dunton . |
| 575,103 | 1/1897 | Burton ............................. 606/201 |
| 2,499,480 | 3/1950 | Fillauer . |
| 2,567,182 | 9/1951 | Cohen . |
| 4,427,007 | 1/1984 | Rexroth ............................. 606/201 |
| 4,760,846 | 8/1988 | Kelly et al. . |
| 4,821,720 | 4/1989 | Hajduch . |
| 4,942,886 | 7/1990 | Timmons . |
| 4,957,105 | 9/1990 | Kurth . |
| 5,307,811 | 5/1994 | Sigwart et al. . |

FOREIGN PATENT DOCUMENTS

| | | |
|---|---|---|
| 2697988 | 5/1994 | France . |
| 11271 | 9/1880 | Germany . |
| 56336 | 5/1891 | Germany . |
| 219012 | 2/1910 | Germany . |
| 258945 | 10/1912 | Germany . |
| 544003 | 2/1932 | Germany ............................. 606/203 |
| WO9221297 | 12/1992 | WIPO . |

*Primary Examiner*—Gary Jackson
*Assistant Examiner*—William Lewis
*Attorney, Agent, or Firm*—Haugen and Nikolai, P.A.

[57] ABSTRACT

The present invention provides a compression device for selectively applying compressive force to a localized area of interest on the surface of a body that is readily positioned and fastened in place. The device includes a resilient compressible element positioned on a relatively rigid member associated with a clamping frame that at least partially surrounds a limb or other body area of interest. An adjustable closure means is provided for adjustably completing the clamp arrangement to completely enclose said bodily region of interest in a manner that enables the compressible element to be applied to the precise site of interest. The adjustable closure element permits accommodating bodily parts such as limbs of various size and facilitates adjustment of the compressive pressure applied. The device may take a variety of embodiment forms.

19 Claims, 2 Drawing Sheets

SELECTIVE VASCULAR COMPRESSION DEVICE

BACKGROUND OF THE INVENTION

I. Field of the Invention

The present invention is directed generally to a simplified adjustably fastened, quickly positioned external pressure delivery device for applying varying amounts of localized external pressure to a selected region of the body. More particularly, the invention relates to a portable, wearable vascular compression device for promoting hemostasis at the site of a puncture after a vascular catheterization procedure has been performed which applies adjustable localized pressure at the exact site of interest for a required time that minimizes interference with patient mobility. The device and method are particularly suited to access the radial artery in the forearm.

II. Related Art

Today, numerous medical procedures for the purpose of both diagnosis and treatment are undertaken and enabled by navigation of the vascular system of the patient. These procedures are performed in connection with diseases of the vessel system including heart catheterization and angiography and the investigation or treatment of other malformations or diseases in organs, such as the brain or kidneys. Each such procedure typically begins with the provision of a small incision in the accessing artery or vein using a small diameter cannula. A guide catheter device is normally inserted into the cannula extending into the arterial or venial passage of interest, and the operative catheter is thereafter threaded over the guide device into the vascular system. After the procedure is completed, the catheter is withdrawn and the guide and cannula removed, leaving a wound including an arterial or venial incision which will bleed profusely unless the bleeding is stopped for a sufficient length of time such that clotting occurs and the vascular passage recovers sufficiently that it can again withstand normal blood pressure without leaking. Bleeding has long been arrested manually by the physician or other health professional by applying a compressive bandage utilizing one or more fingers and holding the compress in place manually for a time up to about one-half hour. This is a time-consuming menial task for the health professional and the application of a steady pressure is most difficult and fatiguing.

For some time, many of these procedures have been undertaken via a femoral artery or vein in the groin of the patent. In this regard, several devices have been proposed which address the application of pressure to accomplish hemostasis of a femoral artery or vein following such procedures. One such device is found in published PCT Application WO92/21297, published 10 Dec. 1992, which describes an apparatus for closing operation wounds after the puncturing of a femoral vessel (vein or artery) which has a head-mounted displaceably in a vertical direction on a swing arm of an upright member which, in turn, is fastened to the frame of a hospital bed. This device is quite large, expensive and cumbersome to use and requires the patient to lie immobile in the prone position for the entire time the device is used.

Another device for post-catheterization hemostasis is found in U.S. Pat. No. 4,957,105. This device utilizes hip straps which lead from a pelvic apron up over the hips and over an opposing lip so that tensile force is applied to the femoral site as by a groin strap. An additional device, found in U.S. Pat. No. 5 307 811, includes a belt or strap for fastening around the patient in conjunction with a shaped two-part, slidably-extendable base plate which supports fixed, inflated pressure applying appurtenance attached to the inner or lower side of the relatively rigid base plate. The device is configured to specifically address the frontal femoral region, the belt enclosing the entire body of the patient. That device does not enclose the patient other than by virtue of the strap; and it is apparent that the location of the device will remain stable only as long as the patient remains immobilized in a prone position. Otherwise, the strap may slip out of place and dislodge the device.

The present state of such devices clearly indicates the need for the provision of a vascular compression device that is simpler in construction, easier to apply and more versatile in its use. In addition, because available devices that compress the femoral region generally result in compression that is debilitating to the patient, the trend among physicians has been toward greater use of vessels in the arm, such as the radial artery, to allow the patient to perambulate directly after the procedure. Unfortunately, the state-of-the-art with respect to hemostasis in the radial artery involves the use of a tourniquet which cuts off all blood supply to the distal limb—a most undesirable situation which needs to be addressed by a new device. Thus, a need clearly is present for a device that would be less debilitating and adaptable to perform vascular compression at a variety of puncture sites which might be utilized to access the vascular system of the patient, including particularly the radial artery in the forearm or wrist.

Accordingly, it is a primary object of the present invention to provide a low cost device for applying varying degrees of localized external pressure to a bodily region of interest such as the site of a vascular intervention procedure that is of relatively simple construction and which minimizes interference with patient mobility and activities.

A further object of the present invention is to provide a wearable compression device for selectively applying compressive force to a localized surface region of interest in the body that is readily adjustable and portable.

A still further object of the present invention is to provide a compression device for selectively applying varying degrees of compressive pressure force to a localized surface region of interest in the body which does not otherwise impair circulation.

A yet still further object of the invention is to provide a method for selectively compressing a region overlying a vascular structure which minimizes the time required for the health professional to apply, attend and remove.

Another object of the present invention is to provide a device for selectively applying varying degrees of external pressure to a localized area of the forearm or wrist to promote hemostasis in the radial artery.

Other objects and advantages associated with the invention will occur to those skilled in the art in conjunction with further study of this specification and claims.

SUMMARY OF THE INVENTION

The present invention provides a compression device for selectively applying compressive force to a localized area of interest on the surface of a body that is readily positioned and fastened in place. The device includes a resilient compressible element positioned on a relatively rigid member associated with a clamping frame that at least partially surrounds a limb or other body area of interest. An adjustable closure means is provided for adjustably completing the clamp arrangement to completely enclose said bodily region of interest in a manner that enables the compressible element to be applied to the precise site of interest. The adjustable closure element permits accommodating bodily parts such as limbs of various size and facilitates adjustment of the compressive pressure applied. The device may take a variety of embodiment forms.

One embodiment includes an adjustable clamping frame for surrounding a limb or other bodily region of interest in which the clamping frame includes a pivotally adjustable rigid member hinged at one end to a structurally shaped clamping frame member such that it provides one side of the clamping arrangement when closed toward the bodily region of interest. The free end of the hinged member carries the fixed end of an adjustable closure device, preferably in the form of a strap, which also has a free end that completes the clamping arrangement by attachment to the frame as by a hook and loop arrangement. The rigid hinged member further carries a resilient raised compressible element extending away from its surface so that the element provides a lone point of contact along the hinged rigid member when it is closed against the body. Location of the resilient compression element may be adjusted along the length of the rigid member. Non-slip surfaces may be provided in parts of the remainder of the clamping frame to prevent slippage once the device is secured in place. A plurality of hinge sites or snap-in joint sockets can be provided in the clamping frame member to provide for a variety of limb sizes.

Another embodiment includes a single rigid clamping frame shaped member designed to enclose a portion of the circumference of the bodily part to be addressed and also carries a resilient compressive element for applying localized pressure. An adjustable strap designed with the shaped member to circumferentially capture the limb or other bodily part is permanently attached at one end to the rigid frame member and adjustably, as by a hook and loop system, attaches to the other end of the rigid frame member to complete the enclosure.

In yet another embodiment, a rack and slider system is provided that includes a slidably attached adjustable ratcheting member or slider which forms a "C" clamp arrangement with an L-shaped member carrying a rack having a plurality of teeth. The closure of the "C" is accomplished by a strap member rigidly attached at one end to the free end of the ratcheting slider member and, utilizing a hook and loop system, or the like, the other end is fastened to the L-shaped member. A resilient compressible bulb located on the inward directed surface of the ratcheting member addresses and provides the localized compression at the spot of interest.

The device contemplated by the invention is normally in the range of about 2–3 cm in width for use about an arm or wrist but may be made any convenient size with respect to the girth of the part to be addressed. While any convenient material may be used for the rigid sections, clear plastic material such as plexiglass, semi-rigid polyethylene terephthalate (PET) or the like are preferred so that the state of the locus addressed by the resilient member can be adequately perceived with the device in place. Non-slip surfaces, as desired, may be provided in the inner surfaces of other rigid portions that contact the body. The system may be configured to address any particular arterial or venial site so accessible; but particular suitability is associated with the veins and arteries of the arms, particularly the radial artery.

BRIEF DESCRIPTION OF THE DRAWINGS

In the drawings, wherein like numerals depict like parts throughout the same.

DETAILED DESCRIPTION

The present invention provides a simple, readily applied convenient compression application system for applying localized compressive force to a specific point on a limb of the body such as occasioned for the closure of an arterial or venal incision accompanying a catheterization or other invasive vascular procedure. The arrangement is simple, easy to apply and the device may be designed to be cleaned and reused but is inexpensive and so may be more practical as a disposable device. The device is clearly labor-saving and affords the patient single-point compression therapy obviating any general reduction in circulation with respect to the limb of interest. The device, in most instances, does not reduce the mobility of the patient while closure of the vascular incision is accomplished.

Figure 1:
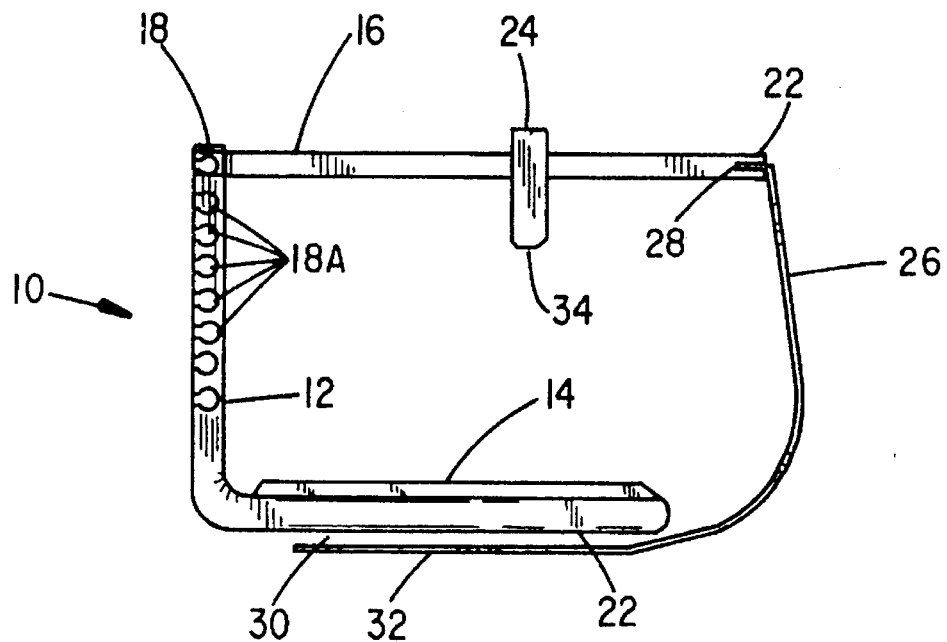
FIG. 1 is a side view of a preferred embodiment of the selective vascular compression device of the invention in the closed position.
Figure 2:
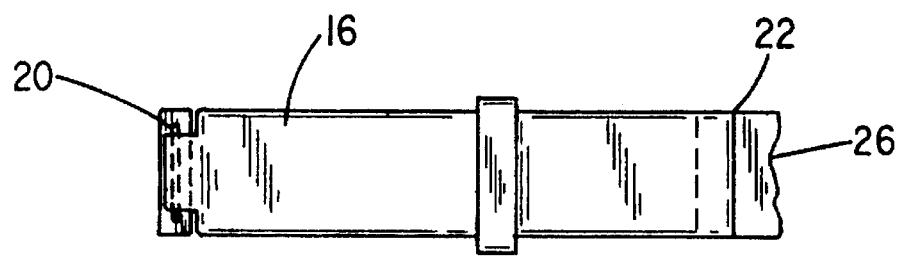
FIG. 2 is a top view of the device of FIG. 1.

FIG. 1 illustrates a preferred embodiment of the device which is shown generally at 10 and which includes a relatively rigid shaped member 12 which may carry a non-slip pad as at 14 on a portion of its inner surface. A relatively rigid member 16 is affixed by hinges at 18 to the member 12 possibly using a hinge pin as at 20 (FIG. 2). Optionally, if desired, the member 12 may be provided with a plurality of additional selectable spaced snap-in socket location for selective snap-fit hinge locations 18A so that the member 16 may most advantageously accommodate the size of the limb or other body area to be addressed. In this manner, for example, the use of a lower hinge location 18A may be desirable when addressing a particularly thin wrist. The hinged member 16 in this embodiment can be attached at any of the several locations 18, 18A, as by snapping into place using the hinge pin, in the manner of attaching a watch band or the like. The member 16 has a free end 22 and carries a raised resilient force applying element 24 which surrounds the member 16 and is slidably adjustable therealong. The resiliency of the member 24 also acts in the manner of a rubber band to keep it in any location once set along the length of the member 16. A strap 26 is fixed to the free end 22 of the member 16 as by being adhesively or compressively inserted with a slot 28 and extends around so as to comfortably overlap the member 12 as at 30 where it can be adhered thereto at any point as by a hook and loop system, a portion of which is shown at 32 as being adhered to the surface of the member 12.

Hinged member 16 together with the strap 26 allow the device 10 to be opened and closed such that the device can be clamped around any limb or other portion of a body if made a compatible size. The hinged member 16 is leveraged by the strap 26 to enclose the portion of the body of interest and the resilient compressive force applying device 24 adjusted along the member 16 to the exact spot to be treated. As can be seen in FIG. 2, the assembly can be made quite narrow, i.e., about the width of a watch band (2–3 cm), for example. It should further be noted that the pressure applying member 24 projects a distance away from the member 16 as at 34 so that when the clamping system is closed utilizing the strap 26 about an arm or wrist, for example, the only contact along member 16 with the body is in the form of the outer surface 34 of the resilient member 24 otherwise allowing unrestricted blood flow in the limb making the use of the device more comfortable to the patient. The hook and loop system or other type strap together with the non-skid member 14 further cooperate to maintain the position of the device on the patient as desired. Of course, the pressure delivered to the situs of interest by the resilient member 24 can be easily adjusted by adjusting the enclosure strap 26 along the hook and loop strip 32.

Figure 3:
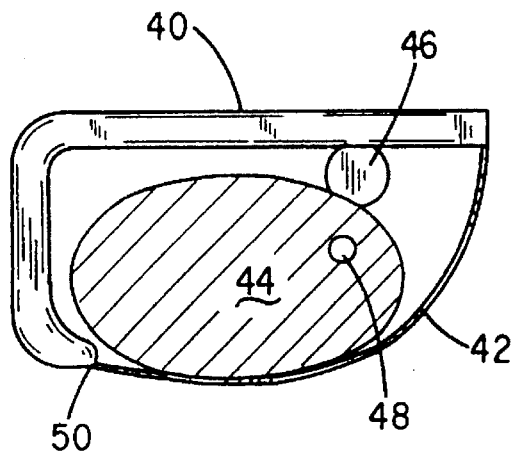
FIG. 3 is a side view of an alternate embodiment of the selective vascular compression device of the invention.

FIG. 3 depicts an alternate embodiment in which a relatively rigid structurally L-shaped or modified L-shaped member 40 cooperates with an adjustable closure strap 42 to surround and enclose a limb such as a forearm or wrist 44. In this embodiment, the resilient, compressible force applying element 46 is depicted as a bulb shape which may be silicon rubber or other benign resilient material. In FIG. 3, it is depicted as addressing the radial artery 48 in forearm or wrist 44. Note that the shaped member 40 contains gently curved inner surfaces as at 50 to minimize the discomfort of contact as with the limb 44. The strap 42 may be adjustably attached to the member 40 using a hook and loop system, for example, such as that associated with the embodiment of FIG. 1.

Figure 4:
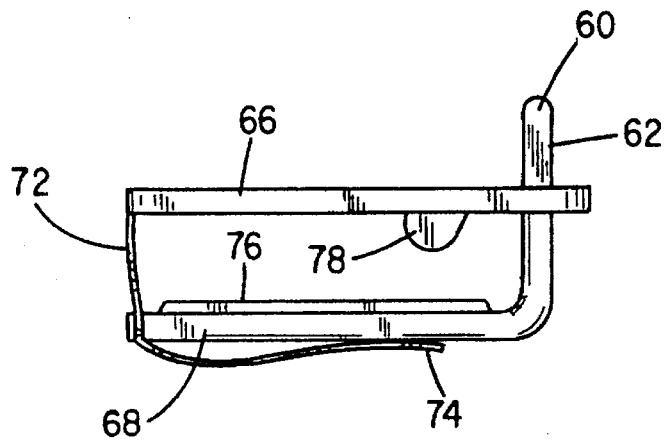
FIG. 4 depicts a side view of yet another embodiment.
Figure 5:
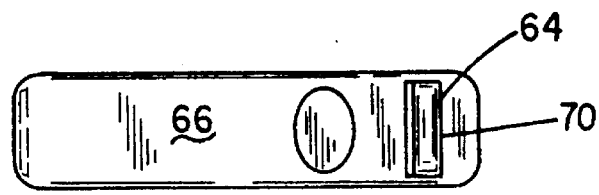
FIG. 5 is a top view of the embodiment of FIG. 4.

FIGS. 4 and 5 depict yet another embodiment of the device which, as can be seen from the Figures, may take any of many forms within the spirit of the present invention. Thus, in FIG. 4 there is shown a relatively rigid L-shaped structural member 60 which may be somewhat similar to the member 12 in the embodiment of FIG. 1 in overall shape but which contains a series of downward directed ratcheting teeth in the form of a rack on an outer surface. These cooperate with a mitered opening 64 in a relatively rigid slider or clamping element 66 in a manner such that when addressing the member 60 at an acute angle therewith, the opening 64 slides over the member 60 but when the free end of the member 66 is closed toward the lower portion 68 of the member 60 such that it approaches being parallel therewith, the upper edge 70 of the mitered opening 64 engages the adjacent one of teeth 62 thereby preventing upward dislocation of the member 66 relative to the member 60. The position of the member 66 relative to the leg 68 of the member 60 is maintained as by an adjustable strap member 72 which, as was the case in other embodiments, may be fastened to the lower surface of the leg 68 as by a hook and loop system at 74. A non-slip surface 76 may also be applied to the leg 68 of the structural shape 60 and the member 66 may carry a bulb-shaped resilient compression delivering member 78 or a slidably adjustable member such as that depicted at 24 in the embodiment of FIG. 1.

In this manner, localized compressive pressure can be pinpointed to almost any location on a limb or possibly other bodily area of interest in the manner which minimizes patient discomfort, professional health care labor and unwanted accompanying effects. Pressure is applied and healing is achieved without the use of any kind of a tourniquet or without requiring a health care professional to manually apply pressure for a long period of time. The device can simply be clamped about the area of interest and the resilient compression device adjusted to exact location desired and the strap secured in place such that the desired amount of pressure is applied by the resilient device at the site of interest.

Because the relatively rigid portion of the device is shaped to at least partially enclose about the limb or other body part addressed, the clamping device of the invention remains stably positioned once tightened and allows for maximum patient mobility. Even a version sized to address the femoral region, for example, would not require the entire body to be engaged (only the proximal limb) and would permit the patient at least minimal ambulatory mobility while the device was in place about one leg. The shape of the frame member or members, as the case may be, stabilizes the device so that once properly positioned, it will not easily slip or be dislodged by motion of the patient. The pressure application, i.e., the resilient element of the device, preferably is one which does not require inflation but which relies on its own compressible and resilient nature with the adjustable strap member to provide the necessary adjustability in the amount of pressure applied. In this manner, the device of the invention is simple, lightweight and portable. It requires no internal devices for application, use or removal.

The relatively rigid portions of the device of the invention are preferably fabricated of a transparent plastic material such as plexiglass or polyethylene terephthalate (PET), or the like. Transparency allows one to monitor more closely the positioning of the compression device and the ongoing situation at the wound. The strap or belt may be made of any convenient woven material and some degree of elasticity may be provided in the strap if desired.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications can be accomplished without departing from the scope of the invention itself.

We claim:

1. An adjustable device for selectively applying localized compressive force to a body surface area of interest comprising:
   (a) an adjustable clamping frame for adjustably enclosing a limb or other body region of interest, said clamping frame including a pivotally adjustable hinged member for closing on said region of interest forming one side thereof and an adjustable closure means for removably retaining said hinged member in a clamping position;
   (b) a force applying resilient element carried by and positioned on said hinged member; and
   (c) resilient, non-slip pad means on at least a portion of a surface of said clamp frame means contacting the body.

2. The device of claim 1 wherein said resilient element is a polymeric band mounted over and slidable along said hinged member.

3. An adjustable device for selectively applying localized compressive force to a body surface area of interest comprising:
   (a) an adjustable clamping frame for adjustably enclosing a limb or other body region of interest, said clamping frame including a pivotally adjustable hinged member for closing on said region of interest forming one side thereof and an adjustable closure means for removably retaining said hinged member in a clamping position;
   (b) a force applying resilient element carried by and positioned on said hinged member; and
   (c) wherein said clamping frame includes a plurality of sequential locations for attachment of said hinged member along one dimension thereof to thereby adjust the size of that dimension of the region of interest to be addressed by the adjustable device.

4. The device of claim 3 wherein said clamping frame has a height and width and said plurality of locations for attaching said hinged member allow the height of the frame to be adjusted.

5. The device of claim 3 wherein said device is entirely portable.

6. The device of claim 5 wherein said clamping frame is of a size to enclose a forearm.

7. The device of claim 3 wherein the position of said force applying member is adjustable along the length of said hinged member.

8. The device of claim 3 wherein said hinged member has a hinged end and a free end wherein said adjustable closure means is a strap member having a fixed end attached to the free end of said hinged member and a free end adjustably and removably attachable to said clamping frame and with said clamping frame completely enclosing said region of interest and leveraging pressure applied from said hinged member.

9. The device of claim 8 wherein said strap member is removably attached to said clamping frame as by an hook and loop system.

10. The device of claim 3 wherein said resilient element protrudes above the surface of said hinged member toward said body region such that only said resilient element contacts the body along the length of the hinged member when the device is in place.

11. A device for applying external pressure to a site in a bodily region of interest such as the site of an invasive vascular procedure comprising:

(a) a clamping frame shaped to address and at least partially enclose a limb, or other body area of interest;

(b) a compressible resilient element for applying external pressure to a localized bodily region of in interest carried by said clamping frame;

(c) adjustable reattachable closure means for attaching said clamping frame to said bodily region of interest in a manner that enables precise positioning and retention of said compressible element at said bodily site; and (d) wherein said clamping frame is a single member.

12. The device of claim 11 wherein the resilient element is a bulb of silicon rubber.

13. The device of claim 11 wherein said clamping frame is attached to the body by a strap member that attaches between ends of said clamping frame.

14. A device for applying external pressure to a site in bodily region of interest such as the site of an invasive vascular procedure comprising:

(a) a clamping frame shaped to address and at least partially enclose a limb, or other body area of interest;

(b) a compressible resilient element for applying external pressure to a localized bodily region of interest carried by said clamping frame;

(c) adjustable reattachable closure means for attaching said clamping frame to said bodily region of interest in a manner that enables precise positioning and retention of said compressible element at said bodily site; and (d) wherein said clamping frame includes an L-shaped structure carrying a rack of angled teeth along one side thereof and a planar slider member having first and second ends and an opening toward said first end adapted to fit over an end of said L-shaped structure, the opening further being mitered to cooperate with said teeth to adjustable retain said first end of said planar member with said adjustable closure means retaining said second end.

15. The device of claim 14 wherein said adjustable closure means further comprises a strap having a fixed end attached to said second end of said planar member and a free end removably attachable to said L-shaped member.

16. The device of claim 15 wherein said strap member is removably attached to said L-shaped member by hook and loop system.

17. The device of claim 14 wherein said resilient compressible element is carried on said planar member.

18. The device of claim 17 wherein the resilient compressible element is a polymeric band mounted over a slidably adjustable along said planar member.

19. The device of claim 14 wherein said resilient compressible element is a bulb of silicon rubber attached to said planar member.

\* \* \* \* \*